(12) United States Patent
Wilser et al.

(10) Patent No.: US 8,449,467 B2
(45) Date of Patent: May 28, 2013

(54) HELICAL ACOUSTIC ARRAY FOR MEDICAL ULTRASOUND

(75) Inventors: Walter T. Wilser, Cupertino, CA (US); Stephen R. Barnes, Bellevue, WA (US); Lex Garbini, El Granada, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1466 days.

(21) Appl. No.: 11/605,738

(22) Filed: Nov. 28, 2006

(65) Prior Publication Data

US 2008/0125659 A1    May 29, 2008

(51) Int. Cl.
*A61B 8/14* (2006.01)

(52) U.S. Cl.
USPC .......................................... 600/459; 600/437

(58) Field of Classification Search
USPC ..... 600/437, 459; 73/584, 587, 645; 310/311, 310/322; 367/61, 62, 72, 117, 138, 140, 153–167
See application file for complete search history.

(56) References Cited

U.S. PATENT DOCUMENTS

| | | | |
|---|---|---|---|
| 4,202,050 A | 5/1980 | Klein | |
| 4,515,017 A | 5/1985 | McConaghy | |
| 4,567,895 A | 2/1986 | Putzke | |
| 5,199,437 A | 4/1993 | Langberg | |
| 5,291,893 A | 3/1994 | Slayton | |
| 5,388,584 A | 2/1995 | King | |
| 5,397,301 A | 3/1995 | Pflueger et al. | |
| 5,505,205 A | 4/1996 | Solomon et al. | |
| 5,546,946 A | 8/1996 | Souquet | |
| 5,680,863 A | 10/1997 | Hossack et al. | |
| 5,735,282 A | 4/1998 | Hossack | |
| 5,876,345 A * | 3/1999 | Eaton et al. .................. 600/466 |
| 5,916,168 A | 6/1999 | Pedersen et al. | |
| 6,059,731 A | 5/2000 | Seward et al. | |
| 6,126,602 A | 10/2000 | Savord et al. | |
| 6,155,979 A | 12/2000 | Moser | |
| 6,159,153 A | 12/2000 | Dubberstein et al. | |
| 6,447,478 B1 | 9/2002 | Maynard | |
| 6,592,520 B1 * | 7/2003 | Peszynski et al. ............ 600/437 |
| 6,676,602 B1 | 1/2004 | Barnes et al. | |
| 6,709,396 B2 | 3/2004 | Flesch et al. | |
| 6,795,374 B2 | 9/2004 | Barnes et al. | |

(Continued)

FOREIGN PATENT DOCUMENTS

WO    WO 2006/119173 A    11/2006

OTHER PUBLICATIONS

Turnbull, DH et al, 'Beam Steering with Pulsed Two-Dimensional Transducer Arrays', IEEE Transactions on Ultrasonics, Ferroelectrics and Frequency Control, vol. 38, No. 4, Jul. 1991.*

(Continued)

*Primary Examiner* — Unsu Jung
*Assistant Examiner* — Daniel Huntley

(57) ABSTRACT

An acoustic array is helical or twisted about or around an azimuth axis. For example, one end of the array has an emitting face at 0 degrees, but the other end has an emitting face at 20 degrees. The elements in between gradually transition between the different rotations. Different apertures of the twisted array may be used to scan different generally radial diverging planes for three-dimensional imaging. The different amount of relative rotation associated with each aperture cause angular elevation spacing of the planes. For use in a catheter, a single row of elements may be used to scan electrically a volume.

21 Claims, 1 Drawing Sheet

U.S. PATENT DOCUMENTS

| | | | |
|---|---|---|---|
| 6,969,354 | B1 | 11/2005 | Marian |
| 7,497,828 | B1 | 3/2009 | Wilk et al. |
| 7,622,853 | B2 | 11/2009 | Rehrig et al. |
| 2004/0111101 | A1* | 6/2004 | Chin .............. 606/151 |
| 2004/0158153 | A1* | 8/2004 | Hirt et al. ............ 600/443 |
| 2006/0173348 | A1 | 8/2006 | Wilser et al. |
| 2007/0066902 | A1 | 3/2007 | Wilser et al. |
| 2008/0125661 | A1 | 5/2008 | Garbini et al. |
| 2008/0287810 | A1 | 11/2008 | Park et al. |
| 2009/0010459 | A1 | 1/2009 | Garbini et al. |

OTHER PUBLICATIONS

Zagzebski, JA, Essentials of Ultrasound Physics, Mosby, Inc., 1996, p. 37.*

PCT International Search Report, mailed Apr. 22, 2008, 6 pages total.

Bom, et al., *Early and recent intraluminal ultrasound devices*, International Journal of Cardiac Imaging, 1989, pp. 79-88, Kluwer Academic Publishers, Netherlands.

Seward, et al., *Transvascular and Intracardiac Two-Dimensional Echocardiography*, Echocardiography: A Journal of CV Ultrasound & Allied Tech., 1990, vol. 7, No. 4, pp. 457-464.

Schluter, et al. *Transesophageal cross-sectional echocardiography with a phased array transducer system Technique and initial clinical results*, Br Heart F, 1982, vol. 48, pp. 67-72.

Crowley, et al., *Optimized ultrasound imaging catheters for use in the vascular system*, International Journal of Cardiac Imaging 4, 1989, pp. 145-151, Kluwer Academic Publishers, Netherlands.

Valdes-Cruz, et al. *Transvascular Intracardiac Applications of a Miniaturized Phased-Array Ultrasonic Endoscope: Initial Experience With Intracardiac Imaging in Piglets*, Circulation, Mar. 1991, vol. 83, No. 3, pp. 1023-1027.

Crowley, et al., *Ultrasound guided therapeutic catheters: recent developments and clinical results*, International Journal of Cardiac Imaging 6, 1991, pp. 145-156, Kluwer Academic Publishers, Netherlands.

* cited by examiner

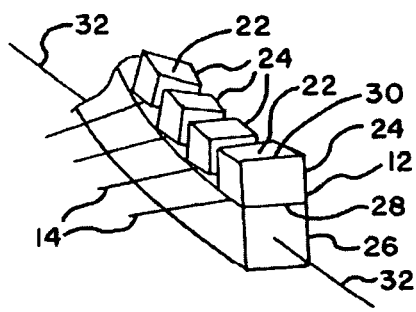
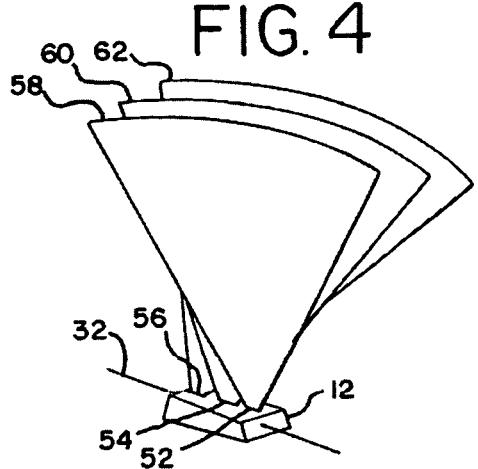
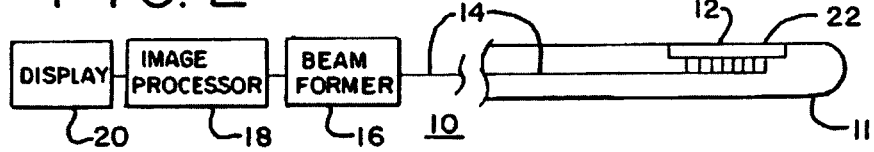
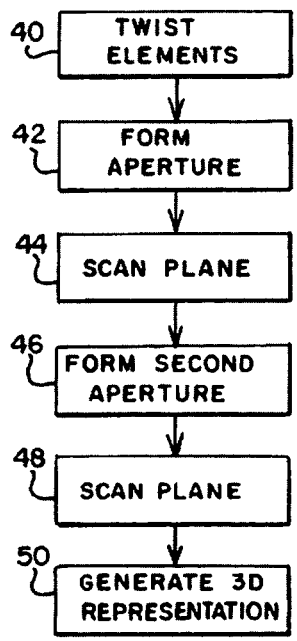
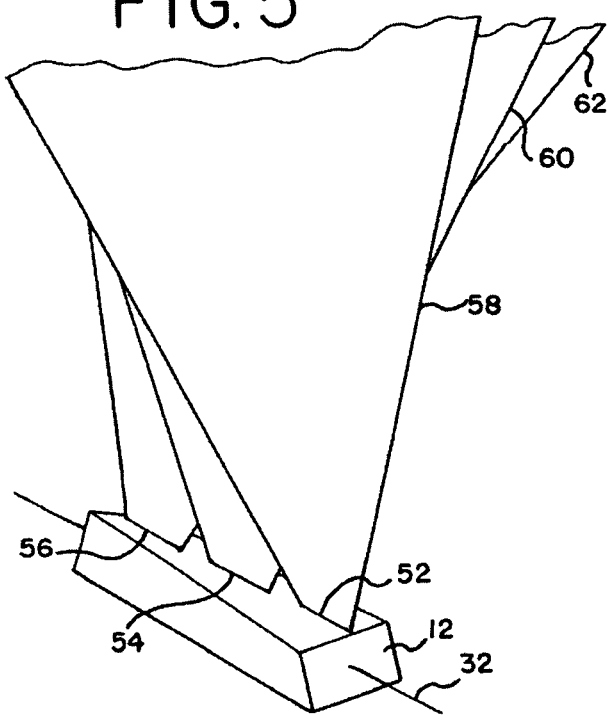

HELICAL ACOUSTIC ARRAY FOR MEDICAL ULTRASOUND

BACKGROUND

The present embodiments relate to acoustic arrays for medical ultrasound. Acoustic arrays are formed from semiconductor or piezoelectric material. Piezoelectric materials include solid piezoelectric or composites. The materials transduce between acoustic and electrical energies.

The material is divided into elements, such as dicing a slab of piezoelectric material into a linear array of elements. By mounting on a rigid or semi-rigid backing, the array of elements maintains a desired planar emitting face. The arrangement of elements may be curved for a curved linear array. For example, an array formed from piezoelectric composite material is warped. The elements on the end are positioned away from an azimuth axis. The emitting face of the array is flat in elevation but curved along azimuth.

Two-dimensional arrays are used for three-dimensional imaging. Transducer material is divided into elements along two-dimensions. However, the number of elements becomes large. An alternative is to steer mechanically in one dimension, such as a one-dimensional array in a wobbler transducer. However, the mechanical steering requires space and adds complexity.

Acoustic arrays may be positioned in a catheter. Due to the size of the catheter, there may be limited space for conductors or mechanical structures. However, the ability to scan in three-dimensions from a catheter is desired, such as for ablation procedures.

BRIEF SUMMARY

By way of introduction, the preferred embodiments described below include methods, systems, improvements and acoustic arrays. The arrays are helical or twisted about or around an azimuth axis. For example, one end of the array has an emitting face at 0 degrees, but the other end has an emitting face at 20 degrees. The elements in between gradually transition between the different rotations. Different apertures of the twisted array may be used to scan different diverging planes for three-dimensional imaging. The different amount of relative rotation associated with each aperture cause angular elevation spacing of the planes or scan regions. For use in a catheter, a single row of elements may be used electrically to scan a volume.

In a first aspect, a system is provided for an acoustic transducer array. A plurality of elements define an emitting face of the array. The elements are spaced along an azimuth axis. Some elements of the array are rotated about the azimuth axis relative to other elements. The emitting face angles in different directions based on the rotation. Electrical conductors connect with respective elements.

In a second aspect, a medical ultrasound transducer includes a plurality of adjacent elements along an azimuth axis. The adjacent elements are arranged in a helix or spiral along the azimuth axis.

In a third aspect, a method is provided for scanning with an acoustic array. A first aperture is formed on an array of elements. The array of elements is twisted about a longitudinal axis. A first plane is scanned with the first aperture. A second, different aperture is formed on the array of elements. A second, different plane is scanned with the second aperture. The position of the second plane corresponds to a different angle of twist associated with the elements of the first aperture than the elements of the second aperture.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a graphical representation of one embodiment of a portion of a helical transducer array;

FIG. 2 is a graphical representation of the array of FIG. 1 in a catheter;

FIG. 3 is a flow chart diagram of one embodiment of a method for scanning with a twisted acoustic array;

FIG. 4 is a graphical representation of one embodiment of three-dimensional scanning with the array of FIG. 1; and FIG. 5 is a graphical representation showing the scan locations adjacent to the array of FIG. 4.

DETAILED DESCRIPTION OF THE DRAWINGS AND PRESENTLY PREFERRED EMBODIMENTS

Using a helical array twisted along an azimuth axis, different scan planes may be scanned. By walking an aperture along the azimuth axis, the angles of the acoustic planes vary. A volume may be sampled.

In a catheter, the helical array may be used to scan from within a patient. For example, the elevation ends or other portion of the elements lie along a helix (e.g., double helix) where the azimuth centerline is straight. By twisting over a small angle, such as about 28 degrees, a volume may be scanned. By walking the aperture along an axis of the catheter, a volume adjacent to the side of the catheter is scanned. The catheter or other tool is guided using three-dimensional representations generated from the volume scan. The images may assist in guiding for ablation or other procedures.

The twist is set or permanent in one embodiment. Other arrays may or may not be provided, such as an adjacent untwisted array for two-dimensional imaging. In another embodiment, a mechanical or other structure varies the array between a twisted position and an untwisted position. An untwisted linear array may provide higher resolution two-dimensional imaging than a twisted array. The twisted array may allow for three-dimensional scanning.

FIGS. 1 and 2 show a system 10 for an acoustic transducer array 12. The system 10 includes the array 12, conductors 14, a beamformer 16, an image processor 18, and a display 20. Additional, different, or fewer components may be provided. For example, the system 10 includes the array 12 and conductors 14 without the beamformer 16, image processor 18, and/or display 20. These imaging electronics may be in a separate ultrasound imaging system. The transducer releasably connects with the imaging system.

The array 12 is used in a transducer probe, such as a medical ultrasound transducer. The transducer probe is used outside of a patient, such as a handheld transducer probe. Alternatively, the transducer is used within a patient, such as a catheter 11 (shown in FIG. 2), a transesophegeal, vaginal, intercavity, intraoperative, or other probe. The array 12 and conductors 14 are connected with or positioned in the transducer probe. A window or lens is over the array 12 for acoustic scanning from an emitting face 22 of the array from within the probe.

The array 12 has a plurality of elements 24, backing material 26, electrodes 28, and matching layers 30. Additional, different, or fewer components may be provided. For example, two or more matching layers 30 are used. As another example, a chamber is provided instead of backing material 26. The backing material 26 absorbs acoustic energy to limit or prevent reflections received from a back of the array 12. The matching layers 30 provide a more gradual transition between acoustic impedance, minimizing reflection from the boundary between the transducer and the patient. The electrodes 28 interact with the elements to transduce between acoustic and electrical energy. The variation of potential or distance between electrodes 28 across an element causes electrical signal generation or acoustic energy, respectively.

The elements 24 are piezoelectric material. Solid or composite piezoelectric materials may be used. Each element is a rectangular solid, cubic, or six sided, but other surfaces may be provided. For example, the emitting face 22 of one or more elements 32 is concave or convex for elevation focusing or frequency based directivity. Alternatively, a microelectromechanical device, such as a flexible membrane, is used. Any now known or later developed ultrasound transducer may be used. Longer elements in elevation as compared to wavelength may provide increased elevation directivity.

Any number of elements 24 may be provided, such as 64 elements. 128 or other number of elements 24 may allow for more or larger apertures. The elements 24 are adjacent each other, such as having substantially wavelength or less spacing between the centers of adjacent elements 24. For example, the elements 24 have half wavelength spacing with kerfs acoustically separating each element 24. The wavelength spacing is based on a center, average, imaging or other frequency of operation of the array 12. Sparse arrays 12 with greater spacing between elements 24 may be used.

The elements 24 are positioned along an azimuth axis 32. For a one-dimensional array 12, the elements 24 are in a single row along the azimuth axis 32. Thirty-two, fifty or more, sixty-four, one hundred and twenty eight or other numbers of elements 24 may be used. The array 12 may be linear or curved linear. A curved linear array 12 has ends or a middle that extend towards or away from the azimuth axis 32, but the elements 24 are still positioned along the azimuth dimension. Due to the curve, some elements 24 of the array 12 are at different depths or ranges.

Multi-dimensional arrays 12 may be used. For example, two or more rows of elements 24 are adjacent to each other along the elevation dimension. 1.25, 1.5, 1.75 or 2D arrays may be provided. The spacing between elements 24 along the elevation dimension is the same or different than along the azimuth dimension, such as a 2×64 array with half wavelength spacing between all adjacent elements in azimuth. The elements are long in elevation, such as having a 3-20 wavelength elevation width, but may be half wavelength or have other spacing.

The side of the elements 24 covered by the matching layer 30, closer to the region to be scanned, and/or opposite the backing material 26 is the emitting face 22. Acoustic energy is transmitted from and received at the emitting face 22 of the array 12. The angle of acoustic energy relative to the emitting face 22 affects the sensitivity of the elements 24 to the energy. The elements 24 are more sensitive to the energy at normal incidence to the elements 24.

Referring to FIG. 1, some of the elements 24 of the array 12 are rotated. The rotation is about the azimuth axis 32. The azimuth axis 32 extends through the backing material 26, the elements 24, the emitting face 30, or adjacent to the array 12. The rotation forms a helical or spiral pattern of the elements 24. The adjacent elements 24 are arranged in a helix along the azimuth axis 32. One element 24 is rotated by a different amount about the axis 32 than other elements 24. The angle of greatest sensitivity is different for the rotated element 24 as compared to for another element 24. The rotation about the azimuth axis 32 may be in addition to rotation away from the axis 32, such as associated with a curved array.

Each element 24 is rotated by a different amount. For example, the elements 24 at opposite ends of the array 12 are rotated about the azimuth axis by at least 10, at least 15 or other greater or lesser number of degrees relative to each other. The azimuth centerline is straight or may rotate or twist. Greater or lesser total rotation may be used. Each of the elements 24 in between are rotated a different amount to step the rotation between the ends. For example, each element 24 rotates 0.47 degrees as compared to an adjacent element 24 (e.g., 64 elements 24 with 30 degrees total rotation provide 0.47 degrees per element 24). Alternatively, groups of elements 24 are rotated a same amount relative to another element 24 or group of elements 24. For example, half the array 12 is rotated one amount and the other half another amount. Any number of steps may be used, with symmetrical or asymmetrical groupings of elements 12. For example, a center group of elements 24, periodic group of elements 24 or other arrangement of elements 24 face a same direction, but other elements are rotated. In one embodiment, a center half of the elements 24 (e.g., center 64 elements 24) are straight or have a same rotational orientation about the azimuth axis, but one quarter of the elements 24 on each end (e.g., 32 elements 24 on one end and 32 elements 24 on the other end) are rotated in a spiral. The rotation is a single step or a plurality of steps.

In general, a larger aperture in elevation provides increased elevation directivity and narrower elevation beamwidth. By twisting the array in elevation, a sub-aperture of elements is used in concert to form an image plane. The total number of independent beams that can be formed by an array is on the order of the number of elements of an aperture. By varying the total twist relative to the elements angular beamwidth, there is a tradeoff between resolution in azimuth and the elevation angular width of the volume formed.

Material holds the elements 24 in the rotated position. For example, the backing material 26 is cured to position the elements 24. As another example, a frame holds the elements 24 in place. In another example, epoxy or other bonding agent cures against a portion or the entire array 12 to hold the array 12 in position. Other materials and associated structures may be used. For the catheter embodiment, the body of the catheter 11 may twist or rotate to avoid interference with, hold in place or assist in holding in place the rotated elements 24.

The backing material 26, electrodes 28, ground plane, and/or matching layers 30 are deformable, allowing twisting with the elements 24. For example, an array normally used as a linear array may be twisted without further changes in manufacture processes. Alternatively, one or more of these layers are formed after twisting to avoid deformation.

Due to the rotation of the elements 24, the emitting face 22 is angled in different directions. The emitting face 22 is twisted, such as associated with a helix with or without an offset from the axis of rotation. The emitting face 22 is rotated in correspondence with the rotation of the elements 24, such as being rotated about the azimuth axis by at least 10 degrees. The emitting face 22 may be twisted more in one area than another. The twist allows for different apertures along the array 12 to have different angles of optimal sensitivity, defining different scanning planes in rotation about the azimuth axis (e.g., different elevation scanning planes).

The electrical conductors 14 are cables, coaxial cables, traces, wires, flex circuits, wire jumpers, combinations thereof, or other now known or later developed conductor. The conductors 14 electrically connect the electrodes 28 of the array 12 with a connector of the transducer probe or the beamformer 16 (FIG. 2). One conductor 14 is provided for each element 24. Alternatively, fewer conductor 14 than elements 24 may be used, such as for switched apertures, partial beamforming, or multiplexing. The conductors 14 are separately addressable as a single array 12. Each element 24 may be selectively used for a given aperture and associated electronic steering. Alternatively, some elements 24 are useable with only a subset of possible apertures.

In one embodiment shown in FIG. 2, the array 12 is within the catheter 11. The catheter transducer is used for imaging. The images assist in diagnosis, catheter or tool guidance, and/or therapy placement. By including the array 12 within the catheter 11 with the elements 24 in the rotated positions, three-dimensional scanning and image representations may be used. Alternatively, the rotated elements 24 of the array 12 are used in other transducers.

The beamformer 16 includes a plurality of channels for generating transmit waveforms and/or receiving signals. Relative delays and/or apodization focus the transmit waveforms or received signals for forming beams. The beamformer 16 connects with the conductors 14. The beamformer 16 selects an aperture including one, some or all of the elements 24 of the array 12. Different apertures may be used at different times. The aperture is formed by using the elements 24 for transmit and/or receive operations while not using other elements. The beamformer 16 is operable to scan from a plurality of apertures formed by adjacent groups of the elements 24. The apertures may walk through regular increments or skip to different portions of the array 12.

For scanning, the beamformer 16 electronically focuses along the azimuth direction. A plurality of scan lines using an aperture is scanned. During receive operations, the focus may vary as a function of depth. An elevation focus is provided by a lens and/or element sensitivity, or the array 12 is not focused in elevation. In alternative embodiments, the beamformer 16 connects with elevation spaced elements for at least partial electric focusing and/or steering in the elevation dimension.

By scanning from different apertures of the array 12, different planes are scanned. The rotation of the elements 24 positions the scan planes for different apertures at different amounts of rotation about the azimuth axis. Short sections of the array 12, on average, point in different directions offset from sections of the array 12 on either side. For example, the first eight elements 24 of an aperture formed on an array 12 with a total rotation of 32 degrees over sixty four elements 24 rotated by sixty four steps have an angle of −14 degrees. The non-coplanar scan planes of the sequence of eight sequential apertures of eight elements each are at angles of −10, −6, −2, +2, +6, +10 and +14. These eight apertures define eight diverging planes spaced apart in elevation. The diverging planes are stacked adjacent to each other to scan the volume. Using different apertures with some or all elements 24 not in common allows for scanning different planes or regions.

The size of each aperture may be limited by the amount of twist. The useable directivity of the elements 24 within an aperture should overlap, such as overlapping the elevation directivity of the elements 24 at the ends of each aperture. Elevation spaced elements, such as two rows of elements, may allow less twist with electronic assisted steering in elevation to reduce beam spreading and allow longer apertures.

The image processor 18 is a detector, filter, processor, application specific integrated circuit, field programmable gate array, digital signal processor, control processor, scan converter, three-dimensional image processor, graphics processing unit, analog circuit, digital circuit, or combinations thereof. The image processor 18 receives beamformed data and generates images on the display 20. The images are associated with a two-dimensional scan.

Alternatively or additionally, the images are three-dimensional representations. Data representing a volume is acquired by scanning. The processor 18 generates a three-dimensional data set as a function of the scanning by the beamformer. The data of the three-dimensional data set may be interpolated to a Cartesian grid or maintained in a scan format. The relative position of the planes used for scanning may be known or assumed based on the aperture position and rotation of the corresponding elements 24. Any rendering may be used, such as projection, volume, and/or surface rendering. The processor 18 generates the three-dimensional representation from the data representing the volume.

By using the twist of the emitting face 22 of the array 12, different planes within a volume may be scanned. The planes are spaced apart in the elevation dimension, such as extending at different amounts of rotation from the array 12. By electric steering in azimuth, the scans may cover a similar region or have similar extents in the azimuth-range dimension.

FIG. 3 shows a method for scanning with an acoustic array. The method uses the system 10 and/or array 12 of FIGS. 1 and/or 2, or a different array and/or system. Additional, different, or fewer acts may be provided. For example, data representing a volume may be used without generating a three-dimensional representation in act 50. The acts are performed in the order shown, but may be performed in other orders.

In act 40, elements of the array are twisted about a longitudinal axis of the array (i.e., the azimuth axis). The array is twisted into a helix or spiral around the longitudinal axis. The twisting is performed by rotation of the ends of the array, formation of the array in the twisted position, and/or rotation of elements or groups of elements of the array. For example, the array is formed as a linear array with composite elements and kerfs. The backing material is flexible or deformable. The linear array is twisted by any amount. The matching layers and/or electrodes (e.g., flex circuit material) may have sufficient give or be flexible to avoid delaminating by twisting.

The twisted array is held in position by a frame, housing, cured epoxy, guide wires, other structures, or combinations thereof. For example, the array is forced into a corkscrew or helical tool. Epoxy is applied to the array, such as a back of the array. After the epoxy cures, the epoxy maintains the array in the helix. As another example, the array is connected with a memory metal. When the array is heated, the memory metal twists the array and maintains the twisted position even after cooling. In another example, a catheter or other probe body is forced through a mandrel to form a twist or includes a twisted frame. Placement of the array in the body twists and holds the array. In one embodiment, a flat array is twisted while in use for volume scanning and flattened for high resolution scanning. For example, the adjustment in twist during use is provided by twisting wire relative to catheter body, a memory alloy, or forcing a twisted beam through a guide in the backing material.

In act 42, an aperture is formed on the array of elements. The aperture is all of the elements or a subset of the elements. Any size aperture may be used. The aperture includes adjacent elements or is sparse. The aperture is formed by connection of conductors and associated elements to the beamformer. The elements used for transmitting and/or receiving during a given transmit and receive event define the aperture. A different aperture may be used for transmit than for receive.

In act 44, a plane is scanned with the aperture. Using electronic focus, transmit and receive beams are formed using the elements of the aperture. By changing the focus, a planar region may be scanned sequentially using the aperture. Single or multiple beams may be formed for transmit and/or receive operations for each event. Plane wave, diverging wavefront, or unfocused transmission may be used. Different apertures may be used for transmit and receive operations. The scanned plane may include a twist or distortion in spatial position due to the twist of the elements within the aperture. In response to the transmission and reception with the aperture, data representing the scanned region is acquired. The rotation of the elements results in the acquired data representing the region at a particular elevation rotation.

In one embodiment, the scan is from a catheter. The scan may be from other transducer probes.

FIGS. 4 and 5 show the array 12 in a spiral pattern with corresponding apertures 52, 54, 56. For each of the apertures 52, 54, 56, a corresponding generally planar scan region 58, 60, 62, respectively, is scanned. The scan regions 58, 60, 62 are offset from each other in the elevation dimension and are associated with different amounts of rotation about the azimuth axis 32. The planes are adjacent to each other along a dimension substantially orthogonal to the planes (e.g., the elevation dimension). The longitudinal (azimuth) and depth (range) extent of each scan region is similar, overlapping, or different. The elevation angle of each plane is different, such as diverging from a common axis also being the axis of rotation of the array. The intersection of the planes is not in the scanned volume, but instead on or behind the face of the array. Acts 42 and 44 correspond to selecting an aperture and scanning the region associated with the aperture.

In acts 46 and 48, another aperture is formed and the associated region is scanned. By selecting a different aperture, a different plane is scanned. The position of the plane corresponds to a different angle of twist associated with the elements than for other apertures. Other apertures may be formed for scanning other regions or planes. As shown in FIGS. 4 and 5, the planes are spaced apart, but overlap in azimuth and range.

In act 50, a three-dimensional representation is generated. The data obtained from the scan is formatted for rendering. For example, the data is interpolated to a three-dimensional evenly spaced grid. As another example, the data for each plane or scan is scan converted into a two-dimensional data set. The two-dimensional data sets associated with each plane are provided for rendering. In another example, the data is maintained in an acquisition format, such as a polar coordinate format. The known plane positions, sample depth, and scan line position provide relative spatial positioning information for each datum.

The data or associated spatial positions may be warped or adjusted to account for planar skew due to the twisting of each aperture. Since the scan region or plane used to acquire data may bend due to the twist or variation in sensitivity as a function of scan line location, the data may be increased or decreased in amplitude. Interpolation may be used between planes to account for spatial offset. Other warping or adjustments may be used.

The three-dimensional representation is rendered as a function of the data from the scanning. The relative positions of the scan planes are used to format the data and/or for rendering. Any now known or later developed rendering may be used. For example, using either view based diverging lines or parallel lines along a viewing direction, projection rendering is provided. Minimum, maximum, first value over a threshold, average, alpha blending or other projection techniques may be used. Surface rendering may be used. Opacity, shading, or other rendering refinements may be applied.

The result of the rendering is a three-dimensional representation from a given viewing direction. The rendering may be performed from other viewing direction with a same set of data. For real-time imaging, the viewing direction may change for subsequently acquired data sets. Real-time three-dimensional imaging may be provided. The three-dimensional representation is an ultrasound image. The data is B-mode, intensity, Doppler mode, velocity, energy, harmonic mode, contrast agent, combinations thereof, or other types of ultrasound data.

Using the three-dimensional representation, tissue structure adjacent the array may be viewed. In the catheter embodiment, tissue structure of one chamber may be viewed from another chamber or the same chamber. Given the aperture spacing, the near views may provide less volume information for rendering. The array may be positioned a little away from the region to be scanned for higher resolution. The array may be rotated to further increase the volume field of view.

In addition or as an alternative to three-dimensional imaging, two-dimensional images are generated by scanning a single plane or region. Where the array continually twists, the aperture may be limited to scan a single plane. Alternatively, different apertures are used for different scan lines in a twisting plane or region. In other embodiments, a large portion of the array does not twist, so the portion is used for two-dimensional imaging. In yet other embodiments, the array may transition between twisted and non-twisted positions. The array is placed in the non-twisted position for two-dimensional imaging.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for an acoustic transducer array, the system comprising:
   a plurality of elements of a single array defining a single emitting face of the array, the elements spaced along an azimuth axis, some elements of the array rotated, about the azimuth axis in a twisted relationship, relative to other elements, the emitting face angled in different directions based on the rotation;
   electrical conductors connected with respective elements; and
   a catheter for use in a chamber;
   wherein the single array is positioned within the catheter with the elements in the rotated positions, the single array being a one-dimensional array and being an only acoustic transducer array of the catheter.

2. The system of claim 1 wherein the elements are rotated about the azimuth axis in a helical pattern, and wherein the emitting face is twisted based on the rotation.

3. The system of claim 1 wherein elements at opposite ends of the array are rotated about the azimuth axis by at least 10 degrees relative to each other, the emitting face also being rotated about the azimuth axis by at least 10 degrees.

4. The system of claim 1 wherein the plurality includes at least fifty elements along the azimuth axis, each of the elements rotated relative to at least one adjacent element.

5. The system of claim 1 wherein the plurality of elements have wavelength or less spacing in azimuth, and wherein the conductors for each of the elements are addressable as a single array.

6. The system of claim 1 further comprising:
material or device operable to hold the elements at the rotated positions.

7. The system of claim 1 further comprising:
a beamformer connected with the conductors, the beamformer operable to scan different planes from a plurality of apertures formed by adjacent sub-groups of the elements; and
a processor operable to generate a three-dimensional data set as a function of the scanning by the beamformer.

8. In a medical ultrasound transducer, the transducer including a plurality of adjacent elements along an azimuth axis, an improvement comprising:
arranging the adjacent elements in a helix along the azimuth axis such that different groups of elements spaced along the azimuth axis are operable to scan different planar regions stacked in elevation and having similar azimuth extent due to the different groups of elements being spaced along the azimuth axis in the helix.

9. The improvement of claim 8 wherein the adjacent elements define an emitting face of the transducer, the emitting face angled in different directions based on the helix.

10. The improvement of claim 8 wherein elements at opposite ends of the transducer are rotated about the azimuth axis by at least 15 degrees relative to each other.

11. The improvement of claim 8 wherein the plurality includes at least fifty elements along the azimuth axis, an emitting face of each of the elements rotated relative to an emitting face of at least one adjacent element.

12. The improvement of claim 8 wherein the transducer comprises a one-dimensional array.

13. The improvement of claim 8 wherein each of the elements has wavelength or less spacing in azimuth; and
further comprising material or a device operable to hold the elements in the helix.

14. The improvement of claim 8 wherein the transducer comprises a catheter transducer.

15. A method for scanning with an acoustic array, the method comprising the acts of:
forming a first aperture on an array of elements, the array of elements twisted about a longitudinal axis;
scanning a first plane with the first aperture;
forming a second, different aperture on the array of elements, the second aperture corresponding to walking the first aperture azimuthally along the array of elements, the elements of the array being along a same line defined by the elements being twisted about the longitudinal axis; and
scanning a second, different plane with the second aperture, the position of the second plane corresponding to a different angle of twist associated with the elements of the first aperture than the elements of the second aperture;
wherein the scanning of the first and second planes occurs with the array being held in a same twisted position.

16. The method of claim 15 wherein the second plane is adjacent to and non-coplanar with the first plane, the longitudinal and depth extent of the scans of the first and second planes being substantially similar; and
further comprising:
generating a three-dimensional representation as a function of data from the scanning and the relative positions of the first and second planes.

17. The method of claim 15 further comprising:
forming at least a third aperture associated with a third scan plane non-coplanar with and spaced from the first and second scan planes, the relative positions being a function of locations of the apertures on the twisted array.

18. The method of claim 15 wherein the scanning acts comprise scanning from a catheter.

19. The method of claim 15 further comprising:
twisting the array into a helix around the longitudinal axis; and
holding the array in the helix.

20. A method for scanning with an acoustic array, the method comprising the acts of:
forming at least two different, multi-element sub-array apertures from a linear array of at least three elements wherein elevation pointing vectors of the elements in the sub-arrays are different relative to each other; and
scanning a volume with each of the sub-arrays, the scanning comprising scanning different planes, each plane corresponding to a different one of the elevation pointing vectors.

21. The method of claim 20 wherein forming comprises forming the array with an emitting face in a helix.

* * * * *